(12) United States Patent
Koziak et al.

(10) Patent No.: US 10,370,404 B2
(45) Date of Patent: Aug. 6, 2019

(54) PROTOESCIGENIN DERIVATIVE, PROCESS OF ITS PREPARATION, USE OF SAID COMPOUND AND PHARMACEUTICAL COMPOSITION COMPRISING THAT COMPOUND

(71) Applicant: Warszawski Uniwersytet Medyczny, Warsaw (PL)

(72) Inventors: Katarzyna Koziak, Warsaw (PL); Krzysztof Bojakowski, Warsaw (PL); Magdalena Kowalewska, Warsaw (PL); Dorota Maciejko, Warsaw (PL); Oliwia Zegrocka-Stendel, Lomianki (PL); Iwona Grabowska, Biskupiec (PL); Grzegorz Grynkiewicz, Lomianki (PL); Mariusz Marek Gruza, Warsaw (PL); Kamil Jatczak, Pruszków (PL); Katarzyna Filip, Warsaw (PL); Piotr Cmoch, Warsaw (PL); Marta Laszcz, Warsaw (PL); Malgorzata Dutkiewicz, Warsaw (PL)

(73) Assignee: Warszawski Uniwersytet Medyczny, Warsaw (PL)

( * ) Notice: Subject to any disclaimer, the term of this patent is extended or adjusted under 35 U.S.C. 154(b) by 0 days.

(21) Appl. No.: 15/553,301

(22) PCT Filed: Feb. 26, 2016

(86) PCT No.: PCT/IB2016/000187
§ 371 (c)(1),
(2) Date: Aug. 24, 2017

(87) PCT Pub. No.: WO2016/135553
PCT Pub. Date: Sep. 1, 2016

(65) Prior Publication Data
US 2018/0244714 A1    Aug. 30, 2018

(30) Foreign Application Priority Data
Feb. 27, 2015    (EP) .................................... 15000566

(51) Int. Cl.
*A61K 31/58* (2006.01)
*A61P 35/00* (2006.01)
*A61P 37/04* (2006.01)
*C07J 63/00* (2006.01)

(52) U.S. Cl.
CPC ............. *C07J 63/008* (2013.01); *A61K 31/58* (2013.01)

(58) Field of Classification Search
None
See application file for complete search history.

(56) References Cited

FOREIGN PATENT DOCUMENTS

| DE | 10162058 A1 | 7/2003 |
|---|---|---|
| WO | 2005051969 A1 | 6/2005 |
| WO | 2006116656 A2 | 11/2006 |
| WO | 2008028060 A2 | 3/2008 |
| WO | 2012009663 A2 | 1/2012 |
| WO | 2014082286 A1 | 6/2014 |
| WO | 2014104905 A1 | 7/2014 |

OTHER PUBLICATIONS

Z. Zhang, et al., "An Overview of Genus *Aesculus* L: Ethnobotany, Phytochemistry, and Pharmacological Activities" Pharmaceutical Crops, 2010, vol. 1, pp. 24-51.
Committee on Herbal Medicinal Products (HMPC), Assessment Report on *Aesculus hippocastanum* L., semen; European Medicines Agency, Evaluation of Medicines for Human Use; London, Jul. 16, 2009, pp. 1-19.
V.R. Tschesche, et al., "Die Konstitution Des Äscins", Liebig's Ann. Bd. 669, Mar. 28, 1963, pp. 171-182.
G. Wei, et al., "A library of 1,2,3-triazole-substituted oleanolic acid derivatives as anticancer agents: design, synthesis, and biological evaluation", Organic & Biomolecular Chemisrty, 2015, vol. 13, pp. 1507-1514.
S. Rashid, et al., "Synthesis and biological evaluation of ursolic acid-triazolyl derivatives as potential anti-cancer agents", European Journal of Medicinal Chemistry, vol. 66, 2013, pp. 238-245.
R. M. Facino, et al., "Anti-Elastase and Anti-Hyaluronidase Activities of Saonins and Saponins and Sapogenins from Hedera helix, Aesculus hippocastanum, and Ruscus aculeatus: Factors Contributing to their Efficacy in the Treatment of Venous Insufficiency", Arch. Pharm. (Weinheim) vol. 328, pp. 720-724, 1995.
M. Gruza, et al., "Synthesis of Protoescigenin Glycoconjugates with O-28 Triazole Linker", Acta Poloniae Pharmaceutica—Drug Research, vol. 71, No. 6, pp. 959-965, 2014.
International Preliminary Report on Patentability for International application No. PCT/IB2016/000187 dated Aug. 29, 2017.

*Primary Examiner* — Kamal A Saeed
(74) *Attorney, Agent, or Firm* — Young Basile Hanlon & MacFarlane, P.C.

(57) ABSTRACT

Described herein is compound including a protoescigenin derivative having pharmacological properties. Also described are a process of its preparation, and the use of such a compound as a medicament, especially for treating vascular disorders. A pharmaceutical composition comprising such compound is further described.

18 Claims, 11 Drawing Sheets

PROTOESCIGENIN DERIVATIVE, PROCESS OF ITS PREPARATION, USE OF SAID COMPOUND AND PHARMACEUTICAL COMPOSITION COMPRISING THAT COMPOUND

TECHNICAL FIELD

The present disclosure relates to a protoescigenin derivative having pharmacological properties, a process of its preparation, the use of such a compound as a medicament, especially for treating vascular disorders, and a pharmaceutical composition comprising such a compound.

BACKGROUND

Protoescigenin is one of the aglycons contained in saponin mixture known as "escin" which is derived from *Aesculus* family (*Pharmaceutical Crops*, 2010, 1, 24-51). Saponins are classified as triterpene polyhydroxyl glycosides based on four different aglycons (sapogenins) including escigenin, protoescigenin, barringtogenol C and barringtogenol D, differing by substituents at C16/C21 and C24 positions. Up to now, 79 saponines have been isolated from hydrolysates of saponine mixtures.

The composition of saponins mixtures obtained from *Aesculus* family varies and depends on the species and origin of the plant material. Chemical composition of the saponins mixture derived from horse chestnut seeds (*Aesculus hippocastanum* L.) of the tree growing mainly in Europe and North America, suggested by R. Tschesche in Liebig's Ann. 669, 171 (1963) can be depicted by following formula based on *Pharmaceutical Crops.*, 2010, 1, 24-51:

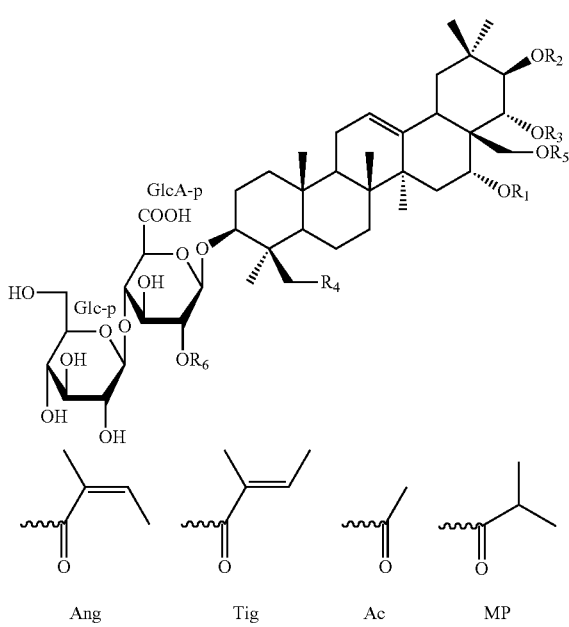

Ang: angeloyl
Tig: tiggeloyl
Ac: acetyl
MP: 2-methylpropanoyl
MB: 2-methylbutanoyl
GlcA-p: β-D-glucuronopyranosyl acid
Glc-p: β-D-glucopyranosyl
Gal-p: β-D-galactopyranosyl
Xyl-p: β-D-xylopyranosyl Horse chestnut extracts have been recognized by ethnopharmacological tradition as a remedy for fever, oedema and hemorrhoidal conditions. Clinical trials confirm that it may be also used in case of chronic venous insufficiency and capillary vessel fragility (EMEA Committee on Herbal Medicinal Products, Assessment Report on *Aesculus hippocastanum* L., semen, EMEA/HMPC/225304/2008, 1 (2009)).

β-Escin is also used as an active ingredient of numerous pharmaceutical preparations which are available on the market. However, from the medical chemistry point of view, β-escin being a complex mixture of many structurally related substances is not a promising material for development of modern medicine. Furthermore, despite the advances in modern analytic and preparatory techniques, it is very difficult to isolate individual components of escin. Thus, the only realistic way to obtain and examine individual mimetics of the natural escin complex mixture is to conduct chemical synthesis and analysis of such newly designed analogs.

WO2005/051969 discloses various compounds obtained from plants of the Barringtonia species which are derived from barringtoside A and barringtoside C as precursor compounds which especially have an arabinopyranosyl substituent at the 21 position which may optionally be further substituted with benzoyl, dibenzoyl, methyl butanoyl, methyl butyryl or tigloyl at the 3 or 4 positions. Alternatively at the 21 position there is tigloyl, benzoyl or dibenzoyl substituents. Said compounds exhibit analgesic properties.

WO2006/116656 describes compositions comprising a triterpenoidal saponin, triterpenoid, triterpenoidal compound or sapongenin, comprising at least two side groups selected from the group consisting of angeloyl groups, tigloyl groups and senecioyl groups, wherein the side groups are attached to carbon 21, 22 or/and 28 of triterpenoidal sapogenin, triterpenoid, triterpenoidal compound or other sapongenin backbones. These compositions are useful for inhibiting tumor cell growth, treating varicose vein disease, venous insufficiency, particularly hemorrhoids or leg swelling.

WO2008/028060 discloses pharmaceutical compositions comprising triterpenoid saponin, triterpenoid, triterpenoid compound or sapongenin, comprising at least two side groups selected from the group consisting of angeloyl groups, tigloyl groups and senecioyl groups, wherein the side groups are attached to carbon 21, 22 or/and 28 of triterpenoid sapogenin, triterpenoid, triterpenoid compound or other sapongenin backbones. These compositions are useful for treating cancer by blocking the migration, metastasis of cancer cells and growth of cancers.

There is still a need for new compounds which are structurally related to the components of saponin mixture, which would have analogous activity but have well defined structure and which would be useful as active agents for modern medicines.

The present invention provides such compounds. The inventors surprisingly found that the newly synthesized protoescigenin derivative exhibits advantageous properties and may be useful as pharmaceutical.

BRIEF SUMMARY

The invention provides a protoescigenin derivative, namely 28-O-{[1-(4-carboxyphenyl)-1H-[1,2,3]triazol-4-yl-protoescigenin of formula (I)

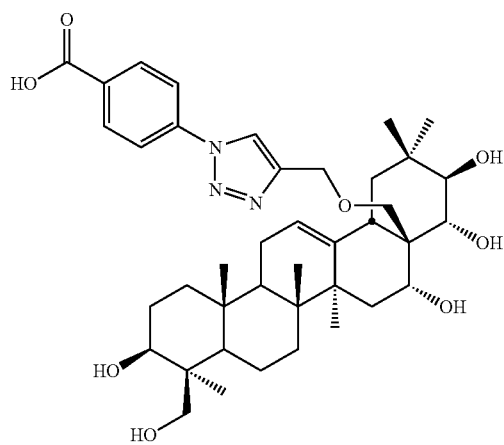

(I)

its salts and isomers. Hereinafter, compound of formula (I) is referred to as the compound of the invention or E-38.

A preferred salt of the compound formula (I) is sodium salt.

In another aspect, the invention also provides a process for preparation of the compound of formula (I) comprising:
a) coupling of 3,24;16,22-O,O-diisopropylidene-28-O-propargylprotoescigenin of formula (II)

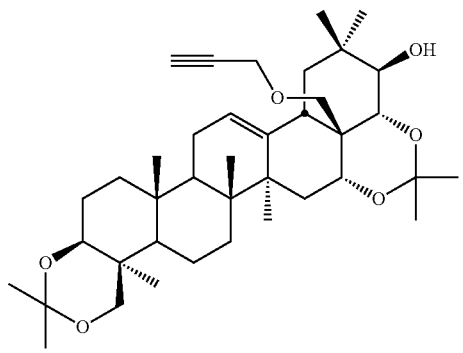

(II)

with 4-azidobenzoic acid of formula (III)

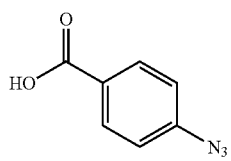

(III)

in the presence of copper (I) cations generated in situ from copper (II) cation in tetrahydrofuran or its mixtures with water b) isolation of 28-O-[(1-(4-carboxyphenyl)-1H[1,2,3]triazol-4-yl)methyl]-3,24;16,22-O,O-diisopropylideneprotoescigenin of formula (IV)

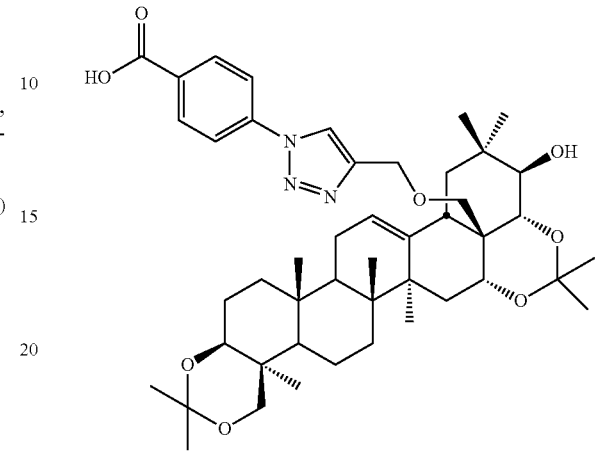

(IV)

from the reaction mixture,
c) purification of 28-O-[(1-(4-carboxyphenyl)-1H[1,2,3]triazol-4-yl)methyl]-3,24;16,22-O,O-diisopropylideneprotoescigenin,
d) preparation of solution or suspension of 28-O-[(1-(4-carboxyphenyl)-1H[1,2,3]triazol-4-yl)methyl]-3,24; 16,22-O,O-diisopropylideneprotoescigenin in solvent selected from group containing $C_1$-$C_3$ alcohol and acetone,
e) reaction with organic acid or inorganic acid and obtaining compound of formula (I),
f) isolation of the compound of formula (I),
g) optional purification of the compound of formula (I), and/or optional transformation of the compound of formula (I) into its salt.

Preferably, copper (I) cations are generated in situ from copper (II) cations by reduction reaction using sodium ascorbate. Preferably, $CuSO_4$ may be used as source of copper (II) cations.

Purification of 28-O-[(1-(4-carboxyphenyl)-1H[1,2,3]triazol-4-yl)methyl]-3,24;16,22-O,O-diisopropylideneprotoescigenin in step c) is preferably carried out by maceration of said compound in methanol in temperature from range from 15 to 40° C., preferably from 20 to 25° C.

Preferably, the C1-C3 alcohol is methanol in step d).

In another preferred embodiment, organic acid p-toluenesulfonic acid is used. Alternatively, hydrochloric acid (HCl) may be used as inorganic acid in step e).

Stage e) is preferably carried out in temperature from range from 15 to 60° C., more preferably from 20 to 25° C.

The optional purification in step g) is preferably carried out in MeOH, THF, acetone or mixtures thereof. In other preferred embodiment the optional purification in step g) may be carried out by maceration of compound of formula (I) in acetone in temperature from range from 20 to 56° C. In another preferred embodiment the optional purification in step g) may be carried out by dissolving compound of formula (I) in mixture of tetrahydrofuran and methanol in temperature from range from 20 to 67° C., cooling down to ambient temperature from range from 15 to 30° C.), precipitating a solid and filtering the solid.

The invention provides also the compound of formula (I), its salts or isomers for use as a medicament.

The present invention provides also the compound of formula (I), its salts or isomers for use in a treatment of vascular disorders, in particular for treating disorder selected from group including venous insufficiency, consequences of ischemia or muscles ischemia/reperfusion, edema, pathological consequences of the presence of arteriovenous fistulas and vascular malformations.

Furthermore, the present invention provides a pharmaceutical composition comprising compound of formula I, its salts or isomers and optionally auxiliary agents.

According to the invention, such pharmaceutical composition is intended for intravenous, oral, rectal or transdermal administration.

Preferably, such pharmaceutical composition comprises additional active agent.

DETAILED DESCRIPTION

Figure 1A:
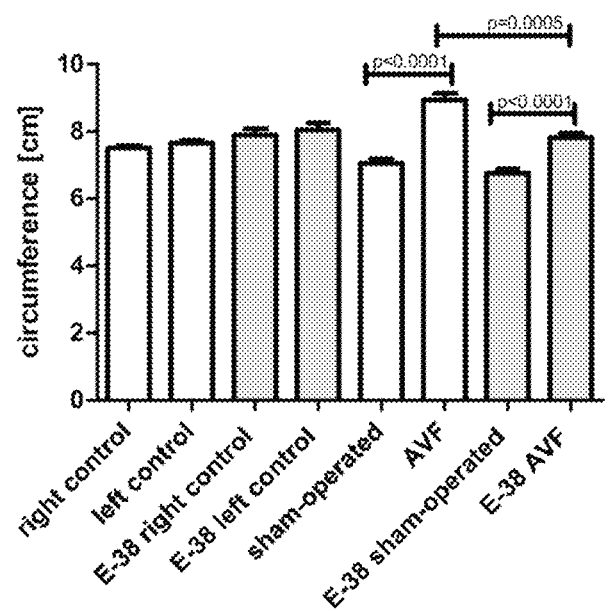
FIG. 1A shows results of measurements of thigh circumference of rats hind limbs in control and experimental group.
Figure 1B:
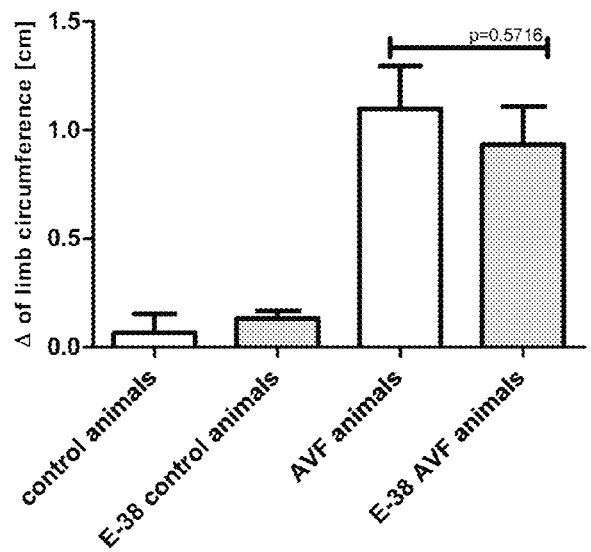
FIG. 1B shows differences between thigh circumference measurements for right and left hind limbs of rats in control and experimental groups.

The present invention provides new protoescigenin derivative of formula (I), which exhibits advantageous pharmacological properties, especially with respect to vascular disorders.

The compound according to the invention may be used in free form or salt form, especially pharmaceutically acceptable salt. Pharmaceutically acceptable salts include, when appropriate, pharmaceutically acceptable base addition salts, for example, metal salts, such as alkali and alkaline earth metal salts, ammonium salts, organic amine addition salts, etc. Examples of metal salts are alkali metal salts, such as lithium salt, sodium salt and potassium salt, or alkaline earth metal salts such as magnesium salt and calcium salt. Examples of ammonium salts are ammonium salt and tetramethylammonium salt. Examples of organic amine addition salts are salts with morpholine and piperidine.

As is evident to those skilled in the art, the compound of the invention contains asymmetric carbon atoms. It should be understood, therefore, that the individual stereoisomers are contemplated as being included within the scope of this invention.

Synthesis Route

The compound of the invention can be produced by known organic synthesis methods. For example, compound of the invention may be produced according to below scheme 1.

Scheme 1

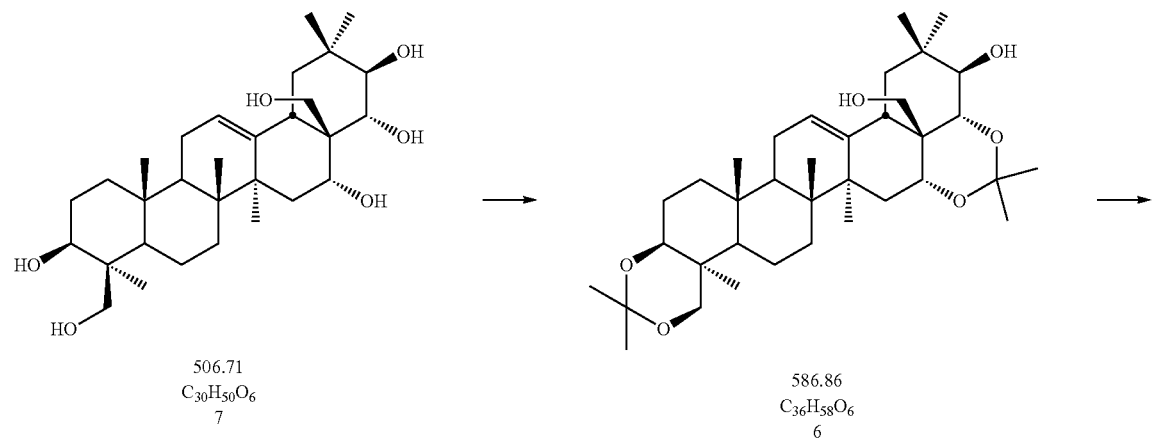

506.71
$C_{30}H_{50}O_6$
7

586.86
$C_{36}H_{58}O_6$
6

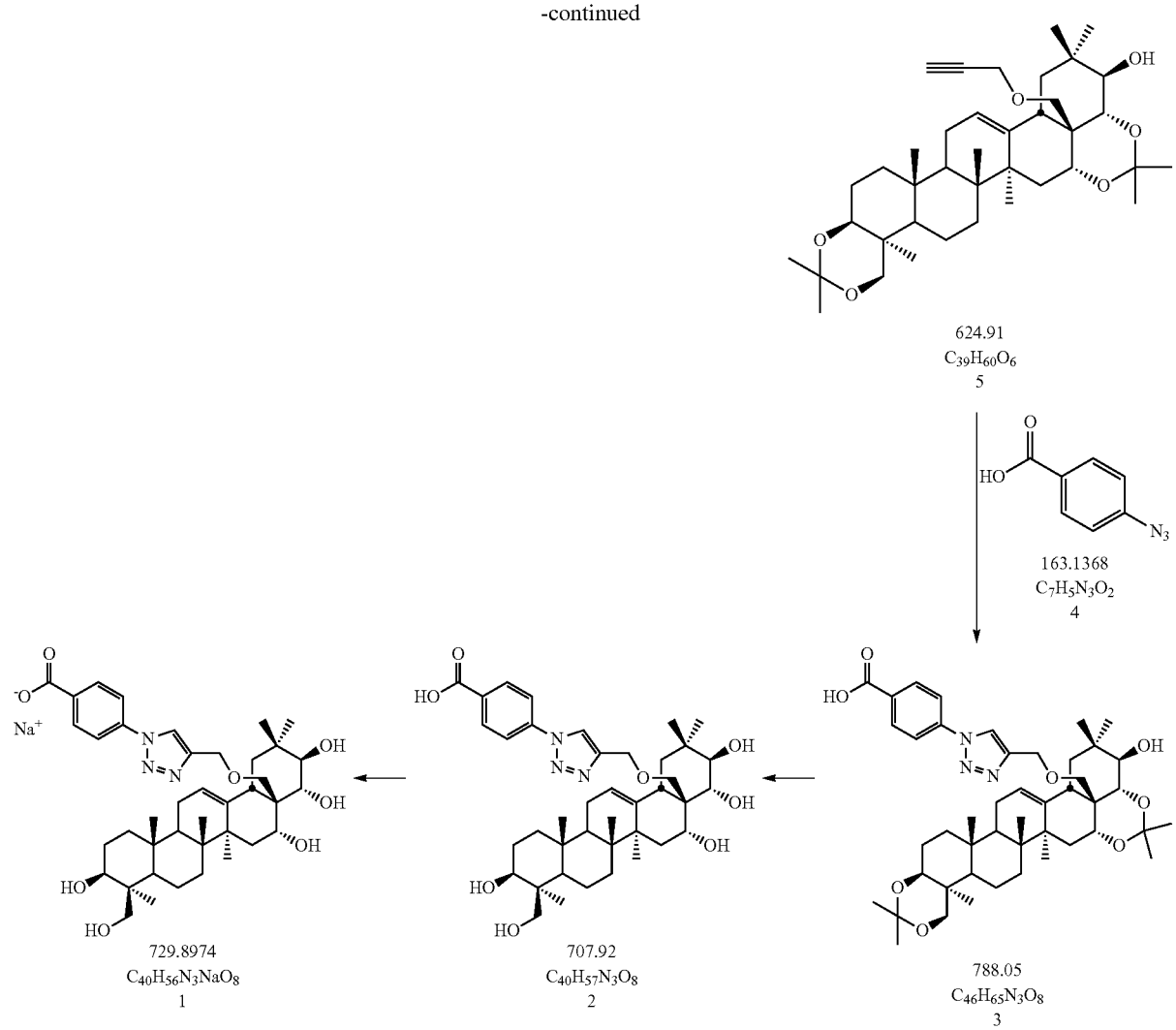

3,24;16,22-O,O-Diisopropylideneprotoescigenin (6)

Preparation of the 3,24;16,22-O,O-diisopropylideneprotoescigenin may be carried out according to the method disclosed in international patent application no. PCT/PL2013/000174 (WO2014/104905). This document is incorporated herein by reference.

3,24;16,22-O,O-Diisopropylidene-28-O-propargyl-protoescigenin (5)

Preparation of the 3,24;16,22-O,O-diisopropylidene-28-O-propargylprotoescigenin may be carried out according to the method disclosed in Jatczak K. et al., Cent. Eur. J. Chem., 2014, 12, 12, 1222-1231 and in Polish patent application no. P.405376. These documents are incorporated herein by reference.

28-O-[(1-(4-carboxyphenyl)-1H[1,2,3]triazol-4-yl)methyl]-3,24;16,22-O,O-diisopropylideneprotoescigenin (3)

Synthesis of the 28-O-{[1-(4-carboxyphenyl)-1H-[1,2,3]triazol-4-yl-protoescigenin 3 may be carried out according to the method described previously in Gruza M. et al., Acta Pol. Pharm.—Drug Res., 2014, 71, 959-965.

However, the method disclosed in said publication was based on a typical Huisgen coupling procedure (CuAAC). Said synthesis method is unsatisfactory and not suitable for use on a large scale. Problematic is the isolation of the crude acid 3 from the reaction mixture and its purification by chromatography.

Therefore, the inventors developed a new method in which the reaction is carried out in mixture of tert-BuOH and water, against the copper(I) ions Cu+ generated in situ from Cu+2 in reduction reaction using sodium ascorbate. For example, $CuSO_4$ may be used as source of copper (II) cations. The inventors surprisingly found that process carried out in THF or THF/water system with $CuSO_4$ instead of $Cu(OAc)_2$ and sodium ascorbate allows for obtaining crude acid 3 in high, over 90%, yield and purity of 70-85% (HPLC).

The next stage of the process is a purification step of the isolated compound. The crude acid 3 was purified by maceration in methanol. The maceration process may be carried out at ambient temperature (15-40° C.) for 1 to 6 hrs. The inventors observed that the best results were obtained when the maceration in methanol is carried out at ambient temperature (20-25° C.) for 2.5-3.5 hrs. Carrying this process in hot methanol causes decomposition of the crude acid 3 into mixture of products.

After purification solids are filtered off, washed with cold methanol, and dried.

Carrying the preparation of the crude acid 3 in the described manner with a purification step gives product of purity over 90% (95-97%) in 75-85% yield.

28-O-{[1-(4-carboxyphenyl)-1H-1-[1,2,3]triazol-4-yl-protoescigenin (2) (the Compound of the Invention, the Compound of Formula I)

The compound 2 may be obtained by cleaving isopropylidene groups in acid 3 in acidic conditions. In general, a method includes preparation of the solution or suspension of the acid 3 in an organic solvent (C1-C3 alcohol, for example methanol or ethanol; or acetone) and the addition of organic or inorganic acid (for example p-toluenosulfonic acid (pTSA), or hydrochloric acid (HCl)). This step may be carried out at temperature from range from 15 to 60° C.

The most efficient variant of the process included treating the suspension of compound 3 in methanol with p-toluenesulfonic acid at ambient temperature (20-25° C.). Crude acid 2 was obtained in 86-90% yield of 90-98% purity (HPLC).

Isolated crude acid 2 may be purified in methanol (MeOH), tetrahydrofurane (THF), acetone or in mixtures thereof. Best results were obtained by the inventors when the purification step was carried out by maceration in acetone (20-56° C.), or by crystallization from refluxed THF-MeOH mixture (20-67° C.), giving pure crude acid 2 in 78-86% yield of purity over 98.5% (HPLC). In the next step mixture may be cooled down to ambient temperature (15-30° C.), and the solids may be precipitated and filtered off.

Sodium salt of 28-O-{[1-(4-carboxyphenyl)-1H-[1,2,3]triazol-4-yl-protoescigenin (1) (the compound of the invention, salt of the compound of formula I)

The acid 2 may be converted into sodium salt 1, by reaction of the acid 2 and sodium hydroxide or sodium alcoholate in alcohol. The inventors have found that the most efficient was to add an equal amount of sodium methanolate to the suspension of acid 2 in ethanol (EtOH) at ambient temperature. The formed sodium salt 1 may be then filtered off, washed with cold ethanol and dried. HPLC analysis confirmed high purity of the obtained material (over 98.7%, usually over 99.5%).

Administration & Pharmaceutical Formulations

As shown below in the Examples, the compound of the invention exhibits interesting pharmacological properties. Furthermore, it exhibits no toxicity and therefore it is a promising candidate for a pharmaceutical.

The compound of the invention may be used in treatment of a disorder, i.e., for the purpose of curing a disorder, but also for the purpose of prevention (as a prophylactic), control, amelioration, or alleviation of any symptom of the treated condition.

The compound of the invention may be normally subject of administration by of any conventional route available in the art. Typical routes include enteral (e.g., oral, sublingual, buccal, nasal, rectal, etc.), parenteral (e.g., intravenous, intraarterial, intramuscular, intracardiac, intradermal intraperitoneal, intrasternal, subcutaneous and intraarticular injection or infusion, etc.) or topical (e.g., buccal, intranasal, rectal, intravaginal, ophthalmic, transdermal, inhalational, etc.) administration. Preferred routes of administration include intravenous, oral, rectal or transdermal.

The compound of the invention may be administered in the form of compositions comprising active compound either as a free compound or, for example a salt, in particular a pharmaceutically acceptable salt, in a pharmaceutically acceptable dosage form. The doses of the compound of the invention in the pharmaceutical or veterinary compositions may be varied so as to obtain an amount of the compound of the invention that is effective to achieve the desired therapeutic response for a particular patient, compositions, and mode of administration.

The selected dosage level will depend upon the activity of the particular compound, the route of administration, the severity of the condition being treated and the condition and prior medical history of the patient being treated.

Besides the compound of the invention, a pharmaceutical composition may also contain at least one additional component typical for the selected dosage form, which facilitates processing the compound of the invention into a pharmaceutical compositions. Such additional components include diluents, excipients, carriers or other suitable auxiliary agents, e.g., fillers (such as sugars, cellulose preparations, calcium phosphates, etc.), binders (such as starch, gelatine, gum tragacanth, methylcellulose, hydroxypropylmethylcellulose, polivinylpyrrolidone, etc.), disintegrating agents (starch, cross-linked polyvinylpyrrolidone, alginic acid, etc.), flow conditioners, lubricants (such as talc, stearic acid and its salts e.g. magnesium stearate, calcium stearate, etc.), glidants, sweeteners, fragrances, preservatives, stabilizers, wetting agents, emulsifiers, solubilizers, osmotic agents, buffers, antioxidants, etc. The skilled person will be able to select appropriate auxiliary agent for specific dosage form.

A pharmaceutical composition of the present invention is intended for parenteral administration by injection or infusion, for example for intravenous administration, suitably include pharmaceutically acceptable sterile aqueous or non-aqueous solutions, dispersions, suspensions or emulsions as well as sterile powders for reconstitution into sterile injectable solutions or dispersions prior to use. Such compositions may be presented in unit-dose or multi-dose containers, for example, sealed ampoules and vials.

Pharmaceutical compositions for oral administration include, e.g., coated and uncoated tablets, pills, capsules, lozenges, as well as solutions, suspensions and powders, granulates and like, used to prepare them.

Pharmaceutical compositions for rectal administration may be present, e.g., in form of suppositories or rectal capsules.

Examples of a pharmaceutical composition useful for topical administration, for example transdermal, include lotions, emulsions, creams, gels, pastes, powders, foams, lipsticks, drops, sprays, solutions and suspensions.

The pharmaceutical compositions of the present invention may be manufactured in manner which is well known in the art. Accordingly, pharmaceutical compositions of the present inventions may be prepared by means of conventional mixing, granulating, dragee-making, dissolving and lyophilizing processes. Selection of appropriate process will depend on the target dosage form.

An appropriate dosage level will generally be about 0.1 to about 33 mg per kg patient body weight per day particularly 0.1, 0.5, 1.0, 1.7, 2.0, 3.0, 4.0, 5.0, 6.0, 7.0, 8.0, 9.0 10.0, 15.0, 20.0, 25.0, 30.0, 33.0, mg per kg patient body weight per day, which can be administered in single or multiple doses.

In case of oral administration, the compositions may be provided in the form of tablets containing 0.01-100% of the active ingredient with respect to the total weight of the composition.

The compounds of the invention may be administered on a regimen of 1 to 4 times per day, preferably once or twice per day. The dosage regimen may be adjusted to provide the optimal therapeutic response.

The compound of the invention may be administered alone or in combination with other active agents. Such additional active agents include, e.g., other medicaments for treating vascular disorders or medicaments for treating conditions which are associated with or induced by vascular disorders. Examples of such medicaments include agents used in treatment of varicose veins, e.g., phlebotropic drugs, medicaments used in case of chronic venous insufficiency (sores), e.g., topical antibiotics, dehydrating drugs. The compound of the invention may be also used in combination with enzymes (topical cleaning of wounds), compression therapy and administration of sclerosing agents into the lumen of varicose veins.

The compound of the invention may be administered to humans but it is also suitable to be used as a veterinary agent, e.g., veterinary active compound, in the prophylaxis and in the treatment of vascular disorders in animals, including farm animals (e.g., cows, pigs, horses, sheep, goats, etc.) as well as pets (e.g., dogs, cats, mice, hamsters, rats, rabbits, guinea pigs, etc.)

For use of the active compounds of the present invention as a veterinary agent, the dosage will, of course, vary depending upon the size and age of the animal and the effect desired. Compounds of the invention used as veterinary agents may be administered in drinking water or in feed, but also orally or parenterally, e.g., in the form of oral or parenteral compositions.

Data obtained from conducted experiments indicate that the use of the compound of the invention can be effective in the treatment of vascular disorders. In particular, group of vascular disorders include, without limitation, venous insufficiency, edema, pathological consequences of the presence of arteriovenous fistulas such as Parkes Weber syndrome and vascular malformations.

Chronic venous insufficiency is a major concern for human health, affecting a significant proportion of adults (approximately 40% of the total population). The most common symptom is the formation of varicose veins in lower limbs, telangiectasia (i.e. spider veins). In most advanced stages chronic venous insufficiency leads to chronic ulcer formation, skin changes—e.g., lipidermatosclerosis. The high incidence and relevance of chronic venous disease has a considerable impact on health care. The cost for treating patients with chronic venous ulcers per year in the United States is estimated to exceed 3 billion USD per year.

Furthermore, the experimental data show that the compound of the invention may be used for treatment of the consequences of ischemia or ischemia/reperfusion in muscles.

The compound of the invention may be also effective in reducing the edema induced by disorders leading to increased venous pressure, e.g., the upper extremity edema in the case of the subclavian vein thrombosis (Paget-Schroetter syndrome) or post-thrombotic syndrome in lower limbs.

Furthermore, the compound of the invention may provide beneficial effects in preventing pathological consequences of the presence of arteriovenous fistulas located in the lower limbs, which causes venous hypertension and peripheral ischemia. Data obtained in conducted experiments show that the compound of the invention causes inhibition of the pathological limb hypertrophy (including reduction in bone growth, a reduction in growth of the limb, a reduction in muscle growth). One of the diseases in which abnormal growth of limb caused by arteriovenous venous fistulas is observed, is Parkes-Weber syndrome. Obtained experimental data suggest that use of the compound of the invention can inhibit hypertrophy and abnormal operation of the limb.

Parkes Weber syndrome (PWS) mentioned above is an example of a vascular disorder in case of which there is no efficient treatment available at the moment. This syndrome has been described in 1907, and is characterized by varicose veins, enlarged limbs and presence of arteriovenous fistulas (AVF). The existence of AVF distinguishes PW syndrome from the Klippel-Trenaunay syndrome, known also as the capillary-lymphatic-venous malformation, CLVM.

The symptoms of PWS are congenital and present at birth. Vascular anomalies affect multiple limbs, less often trunk. Capillary malformations, forming geographic patterns, are commonly located on lateral side of the limb, buttocks or trunk. Additional laterally located veins appear in older age, which may be a consequence of vein anomalies and insufficiency of the deep venous system. Vein malformations in PW syndrome probably result from mutations in the RASA1 gene, which affects normal development of vascular system. In 50% of cases the hypoplasia of lymphatic system is also present and is manifested by lymphatic edema and isolated lymphatic macrocitosis.

The overgrowth of a limb is present at birth, whereas, the axial overgrowth can enlarge while growing. In some cases the lower extremity can be shortened and contralateral hand or foot can be enlarged due to high adipose tissue content, in some cases without skin spots related to capillary malformations. When the pelvis is affected, often as a result of malformations in lower extremity, PW syndrome can be asymptomatic. As a consequence of arteriovenous leak, PW syndrome can lead to cardiac system failure or to limb ischemia.

The treatment of patients with PW syndrome is mainly symptomatic. Compression therapy (bandaging and stockings) and massages are used to reduce symptoms of chronic venous insufficiency and lymphatic edema. When recommended, intravascular and surgical procedures are performed. Surgical treatment is difficult and sometimes requires several intravascular procedures, such as embolization, sclerotherapy or classic open operations—arteriovenous fistula ligation. In severe cases of ischemic extremities, amputation is the only therapy.

The use of the compound of the invention may also be beneficial in other syndromes associated with vascular malformations, in which an increase in venous pressure as a result of increased arterio-venous shunt is observed.

Thus, the compounds of the present invention may be useful for treating vascular disorders including, but not limited to, conditions such as venous insufficiency, consequences of ischemia or muscles ischemia/reperfusion, edema, for example edema induced by disorders leading to increased venous pressure, pathological consequences of the presence of arteriovenous fistulas located in the lower limbs such as Parkes Weber syndrome and vascular malformations.

The compound of the invention exhibits pharmacological properties that are similar to those characteristic for β-escin and Horse chestnut extracts. But, in contrast to these substances, it has a well-defined structure and may be prepared in a repeatable manner, for example according of the method described in the examples.

Furthermore, as shown in the examples, the compound of the invention has no toxic properties and exhibits promising biological characteristics.

In consequence, it is a promising candidate for a medicament, especially for treating and preventing vascular disorders.

EXAMPLES

The following examples are intended to illustrate the invention and are not to be construed as being limitations thereto.

Example 1 Synthesis

Materials, solvents and reagents used in the below syntheses were of commercial origin.

Purity of examined compounds was determined using HPLC/UHPLC methods with chromatography system UltiMate™ 3000RS UHPLC (Dionex Corporation, 1228 Titan Way, Sunnyvale, Calif. 94085, USA), equipped with an autosampler and DAD 3000RS detector.

Method A (UHPLC): Chromatography was performed on a Acquity C18 BEH column (1.7 μm, 100 mm×2.1 mm i.d., Waters) maintained at 30° C. using gradient elution with 10 mM ammonium acetate in purified water as solvent A and acetonitrile as solvent B. The flow rate was set at 0.5 ml min$^{-1}$.

Method B (HPLC): Chromatography was performed on a Kinetex XB C18 column (2.6 μm, 150 mm×4.6 mm i.d., Phenomenex) maintained at 50° C. using gradient elution with 10 mM ammonium acetate in purified water as solvent A and methanol as solvent B. The flow rate was set at 1.5 ml min$^{-1}$.

TLC separations were performed on TLC silica gel 60 $F_{254}$ on alumina sheets (Merck). Visualization was performed by UV light (254 and/or 365 nm) and using ceriummolybdate stain.

Specific rotation was calculated from an optical rotation measurement performed on the PERKIN ELMER 341 Polarimeter at wavelength of 589 nm (sodium lamp), at 20° C.

Differential scanning calorimetry (DSC) measurements were carried out by means of the DSC822 with IntraCooler (Mettler Toledo) with following parameters:

aluminum pan 40 μL; N2 Atmosphere, 60 ml/min;
measurement: heating from 25 to 350° C. at 10° C./min; and
sample preparation: accurately weighed samples (5-7 mg) were packed in the aluminum pan with the pierced lid.

The $^1$H and $^{13}$C NMR spectra were recorded in DMSO-d6 solutions with Varian-NMR-vnmrs600 spectrometer (at 298 K) equipped with a 600 MHz PFG Auto XID ($^1$H/$^{15}$N-$^{31}$P 5 mm) indirect probehead. Standard experimental conditions and standard Varian programs (ChemPack 4.1) were used. The $^1$H and $^{13}$C NMR chemical shifts are given relative to the TMS signal at 0.0 ppm. Concentration of solutions used for measurements was about 20-30 mg of compounds in 0.6 cm$^3$ of deutereted DMSO (DMSO-d$_6$). Used abbreviations are: s—singlet, d—doublet, t—triplet, m—multiplet, ov-ov—signals overlapped. Integrals are not presented due to overlapping of the signals in most cases (the $^1$H NMR chemical shifts for all the compounds studied are given as values of the center of multiplets read from $^1$H-$^{13}$C g-HSQC experiments).

Mass spectra were recorded on a MaldiSYNAPT G2-S HDMS (Waters) Spectrometer via electrospray ionization (ESI-MS).

The IR spectra were recorded on the Thermo Scientific Nicolet iS10 spectrometer in the range of 4000-400 cm$^{-1}$, with spectral resolution of 4 cm$^{-1}$. Samples were measured in KBr pellets.

Number references of the compounds in syntheses are taken from Scheme 1.

Example 1A: 28-O-[(1-(4-carboxyphenyl)-1H[1,2,3] triazol-4-yl)methyl]-3,24;16,22-O,O-diisopropylideneprotoescigenin (3)

Two solutions were prepared freshly before use: solution A—2.40 g of CuSO$_4$.5H$_2$O in 45 ml of degassed water, and solution B: 4.55 g of sodium ascorbate in 45 ml of degassed water.

Ether 5 (15.0 g, 24.0 mmol) and 4-azidobenzoic acid 4 (4.14 g, 25.4 mmol) were dissolved in degassed THF (270 ml). Then, solution A (CuSO$_4$.5H$_2$O, 25 ml) and solution B (sodium ascorbate, 25 ml) were added. The reaction mixture became brown immediately, and then turbid. The reaction was continued at ambient temperature for 3 hours and additional portions of solution A (10 ml) and solution B (10 ml) were added. After next 3 hours, TLC control (CHCl$_3$-MeOH, 9:1, product RF=0.34) indicated complete depletion of the substrate. The reaction mixture was concentrated under reduced pressure and the obtained residue was dissolved in chloroform (150 ml) and water (500 ml). The phases were separated and the water phase was extracted with chloroform (3×50 ml). The combined organic phases were washed with 5% aqueous solution of NaHCO$_3$ (50 ml) and dried over anhydrous Na$_2$SO$_4$. After filtration and concentration, solid crude 3 was obtained (23.1 g). The crude acid 3 was suspended in methanol (MeOH) (200 ml) and stirred at ambient temperature for 3 hours, then filtered, washed with cold MeOH and dried to give acid 3 (yield 14.8 g, 85.9%, HPLC 96.39%).

TLC: RF=0.34 (CHCl$_3$-MeOH 9:1); 0.40 (CH$_2$Cl$_2$-MeOH 85:15);

$[\alpha]^{20}_D$=+8.55 (c 1.0, THF);

M.p. (DSC) 184.4° C. (crystallized from THF);

$^1$H NMR (600 Hz, DMSO-d6), δ (ppm): 13.20 (bs, 1H, COOH); 9.04 (s, 1H); 8.14 (BB' J=8.8 Hz, 2H, phenyl); 8.10 (AA', J=8.7 Hz, 2H, phenyl); 4.85 (bs, 1H); 4.77 (d, J=12.8 Hz, 1H); 4.47 (d, J=12.9 Hz, 1H); 4.23 (d, J=4.4 Hz, 1H); 3.82 (d, J=9.6 Hz, 1H); 3.79 (d, J=12.3 Hz, 1H); 3.68 (dd, J=4.6, 9.2 Hz, 1H); 3.36-3.26 (m, ov, 4H); 3.14 (d, J=8.3 Hz, 1H); 3.07 (d, J=11.4 Hz, 1H); 2.40 (dd, J=3.1, 14.2 Hz, 1H, H18); 1.89-1.75 (m, ov, 5H); 1.56-1.38 (m, ov, 7H); 1.35 (s, 3H, CH3); 1.30 (s, 3H, CH3); 1.28 (s, 3H, CH3); 1.23 (s, 3H, CH3); 1.18 (d, J=11.0 Hz, 1H); 1.06 (s, 3H, CH3); 1.04 (s, 3H, CH3); 0.92 (s, 3H, CH3); 0.88-0.85 (m, 1H); 0.77 (s, ov, 3H, CH3); 0.75 (m, ov, 1H); 0.61 (s, 3H, CH3); 0.53 (s, 3H, CH3).

$^{13}$C NMR (150 Hz, DMSO-d6), δ (ppm): 166.3 (CO, COOH); 144.8 ($C_{IV}$ triazole); 139.9; 139.5; 131.1 (phenyl); 130.5 (phenyl); 122.7; 121.8; 119.3; 98.3; 97.7; 75.9; 75.6; 72.7; 69.7; 68.4; 62.7; 62.6; 52.8; 46.6; 44.2; 43.0; 41.0; 40.8; 39.6; 36.7; 35.7; 35.5; 35.4; 35.1; 31.9; 30.33; 30.16; 28.1; 27.8; 25.6; 25.2; 24.2; 24.0; 22.4; 18.0; 17.8; 17.4; 16.2.

HRMS (ESI): calculated for C$_{46}$H$_{65}$N$_3$O$_8$Na [M+Na]+m/z: 810.4669 found m/z: 810.4673.

Example 1B: 28-O-{[1-(4-carboxyphenyl)-1H-[1,2,3]triazol-4-yl-protoescigenin (2) (the Compound of the Invention, the Compound of Formula I)

Acid 3 (11.36 g, 14.42 mmol) was suspended in MeOH (150 ml) and stirred vigorously at ambient temperature. A catalytic amount of p-toluenesulfonic acid (120 mg) was added and the solids were dissolved in few minutes. The reaction mixture was refluxed for 3 hours and the precipitate was formed. After cooling to ambient temperature the solid was filtered off and washed with cooled MeOH, to give acid 2 (yield 8.81 g, 86.3%, HPLC 98.5%).

Acid 3 (500 mg) was dissolved in the mixture of THF (20 ml) and MeOH (3 ml) at reflux temperature. Then 8+10 ml of solvents were distilled off, and the solution was allowed to cool overnight. The formed solid was filtered off and dried to give acid 3 (yield 394 mg, 78.8%, HPLC 99.21%).

$[\alpha]^{20}_D = -0.5$ (c 1.0, DMSO);

$^1$H NMR (600 Hz, DMSO-$d_6$), δ [ppm]: 13.21 (bs, 1H, COOH); 8.87 (s, 1H, CH triazol); 8.13 (BB', 2H, phenyl); 8.08 (AA', 2H, phenyl); 5.12 (m, 1H, H12); 4.92 (m, 1H, probably OH at C3); 4.72 and 4.47 (2×d, J=13.1 Hz, OCH$_2$-triazol); 4.27 (d, J=4.4 Hz, probably OH at C16); 3.91 (m, 1H, H16); 3.80-3.70 (overlapping m, 3H, H21, H22 and one of H24 protons); 3.18 (m, 1H, one of H24 protons); 3.12-3.08 (d, J=8.5 Hz and overlapping m, 2H, H3 and one of H28 protons); 2.84 (d, J=8.5 Hz, one of H28 protons); 2.46 (dd, J=4.0, 14.3 Hz, H18); 2.32 (t, J=13.2 Hz, one of H19 protons); 1.62 (m, 1H, one of H11 protons); 1.54-1.30 (several overlapping m, 7H, one of H11 protons, both H2, one of H10 protons, one of H15 protons, one of H9 protons, one of H1 protons and H7); 1.27 (s, 3H, CH$_3$-27); 1.20-1.08 (overlapping m, 3H, one of H10 protons, one of H15 protons and one of H9 protons); 1.03 (s, 3H, CH$_3$-23); 0.92 (dd, J=4.4, 12.6 Hz, one of H19 protons); 0.84 (2×s, 6H, CH$_3$-29 and CH$_3$-30); 0.81 (overlapping m, one of H1 protons); 0.64 (d, J=12.0 Hz); 0.46 (s, 3H, CH3-25); 0.36 (s, 3H, CH3-26).

$^{13}$C NMR (150 Hz, DMSO-d6); δ (ppm): 166.4 (CO, COOH); 145.5 (C$_{IV}$ triazole); 142.6 (C13); 139.5 (C$_{IV}$ phenyl); 131.1 (2C, CH, phenyl); 130.5 (C$_{IV}$ phenyl); 122.1 (CH, triazole); 121.9 (C12); 119.3 (2C, CH, phenyl); 78.5 (C3); 76.9 (C21); 71.8 (C22); 70.7 (C28); 66.9 (C16); 63.3 (OCH2-triazole); 62.9 (C24); 55.2 (C5); 46.9 (C19); 46.1 (C7); 46.0 (C17); 42.0 (C4); 40.6 (C14); 39.2 (C18); 38.9 (C8); 38.1 (C1); 36.0 (C6); 35.4 (C20); 33.4 (C15); 32.6 (C9); 29.9 (C30); 27.1 (C2); 26.6 (C27); 23.0 (C11); 22.8 (C23); 18.8 (C29); 18.4 (C10); 15.7 (C26); 15.1 (C25).

HRMS (ESI): calculated for $C_{40}H_{57}N_3O_8Na$ [M+Na]$^+$ m/z: 730.4043 found m/z: 730.4044.

M.p. (DSC) 281° C.

Figure 7:
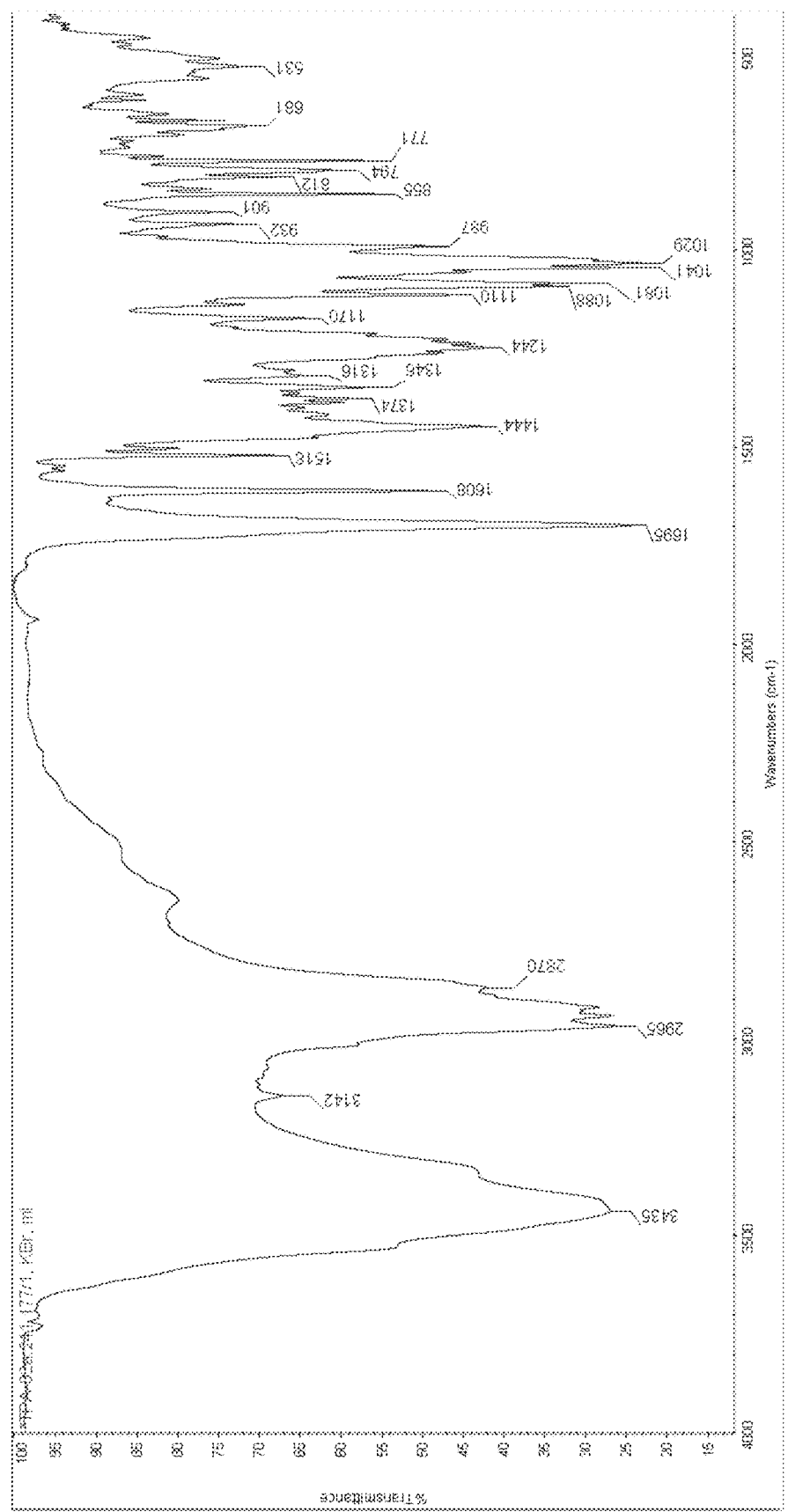
FIG. 7 shows IR spectrum recorded for 28-O-{[1-(4-carboxyphenyl)-1H-[1,2,3]triazol-4-yl-protoescigenin.

IR (KBr) spectra recorded for the acid 2 is presented in FIG. 7.

Example 1C: Sodium salt of 28-O-{[1-(4-carboxyphenyl)-1H-[1,2,3]triazol-4-yl-protoescigenin (1) (the compound of the invention, salt of the compound of formula I)

Acid 2 (8.15 g, 11.51 mmol) was suspended in ethanol (EtOH) (100 ml) and stirred at ambient temperature for 5 minutes. Then sodium methanolate (1.60 g) was added as well as an additional portion of EtOH (100 ml). The solids were dissolved in less than 15 minutes and then a new solid started to form. The reaction was stirred at 65° C. for 1.5 hrs and allowed to cool overnight. The solid was filtered off and washed with cold EtOH (2×25 ml), and dried to give sodium salt 1 (yield 9.31 g, 98.9%, HPLC 99.5%).

Salt 1 (962 mg) was dissolved in MeOH (25 ml) at 45° C. (water bath). The solution was filtered through a filter paper. EtOH was added to the solution and solvents were evaporated under reduced pressure. EtOH (20 ml) was added to the residue and the formed suspension was stirred for 30 minutes, then filtered off, washed with cold EtOH, and dried. The solid sodium salt 1 was formed (yield 787 mg, 81.8%, HPLC 99.61%).

$[\alpha]^{22} = +7.6$ (c 1.0, MeOH);

M.p. (DSC) 253° C.

Figure 8:
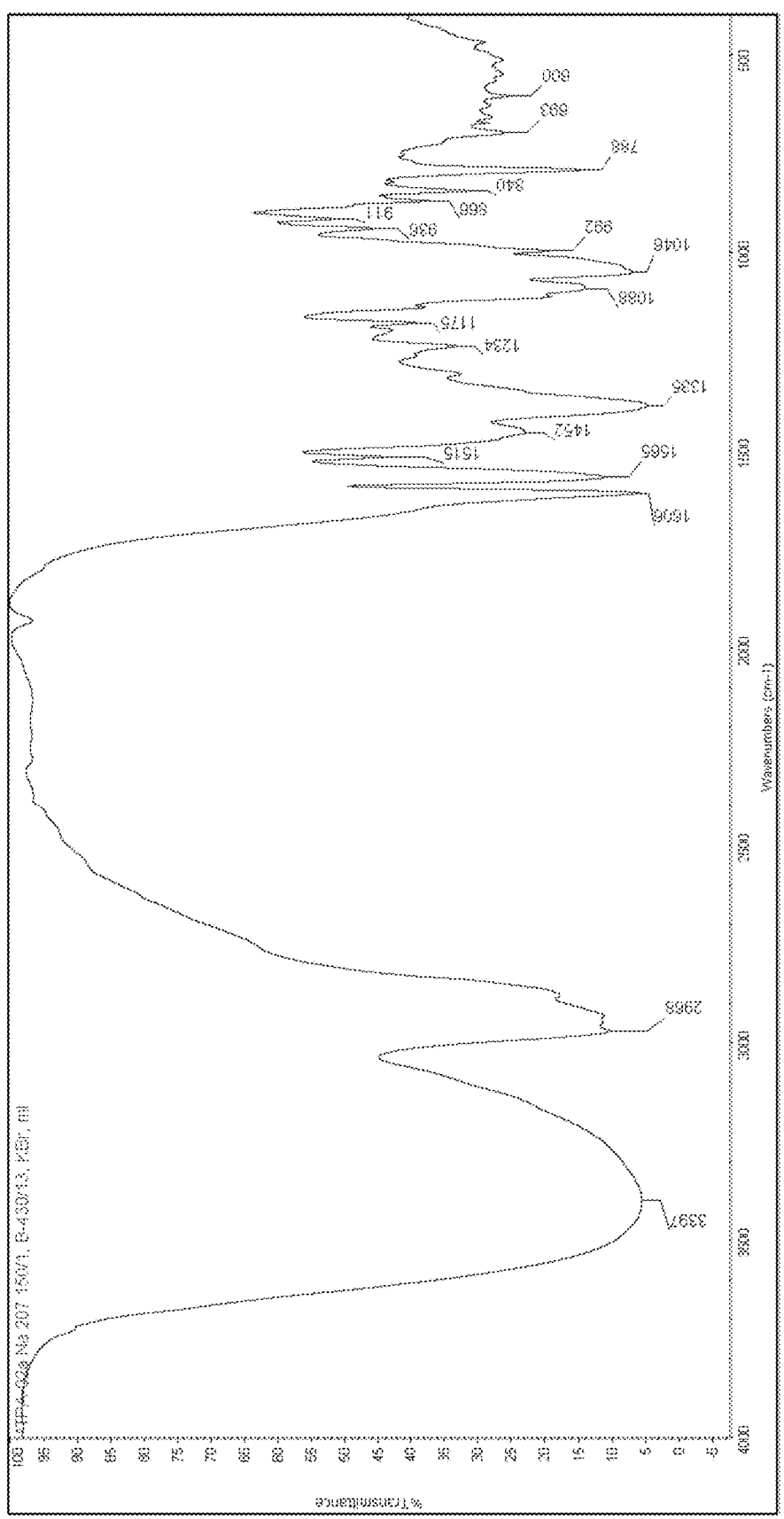
FIG. 8 shows IR spectrum recorded for the sodium salt of 28-O-{[1-(4-carboxyphenyl)-1H-[1,2,3]triazol-4-yl-protoescigenin.

IR (KBr) spectra recorded for the sodium salt 1 is presented in FIG. 8.

Example 2: Pharmaceutical Preparations Comprising the Compound of the Invention

Example 2A: Pharmaceutical Compositions in Form of a Suspensions Containing Compound of the Invention at 10 mg/ml Concentration Composition 1

| Components | Amount [g/L] |
| --- | --- |
| Compound of the invention | 10 |
| Propylene glycol | 150 |
| Sodium Citrate | 1.65 |
| Citric acid | 0.10 |
| Carboxymethylcellulose sodium salt | 5.0 |
| Polysorbate 80 | 1.50 |
| Saccharine | 1.50 |
| Methylparaben | 2.0 |
| Propylparaben | 0.20 |
| Flavor | 1.50 |
| Purified water | Ad 1 l |

Composition 2

| Components | Amount [g/L] |
| --- | --- |
| Compound of the invention | 10 |
| Glycerin | 100 |
| Sorbitol | 100 |
| Polysorbate 80 | 0.30 |
| Xanthan gum | 2.20 |
| Sodium benzoate | 2.00 |
| Sodium Citrate | 0.60 |
| Saccharose | 50.0 |
| Flavor | 1.0 |
| Purified water | Ad 1 l |

Composition 3

| Components | Amount [g/L] |
| --- | --- |
| Compound of the invention | 10 |
| Carbopol 974 P | 30.0 |
| Saccharose | 80.0 |
| Glycerin | 120.0 |
| Sodium hydroxide | 2.0 |
| Benzyl alcohol | 5.0 |
| Flavor | 1.50 |
| Purified water | Ad 1 l |

Example 2B: Pharmaceutical Compositions in Form of Syrups Containing Compound of the Invention at 10 mg/ml Concentration Composition 4

| Components | Amount [g/L] |
| --- | --- |
| Compound of the invention | 10 |
| Hydroxyethylcellulose | 15.0 |
| Sodium citrate | 0.90 |
| Citric acid | 2.80 |
| Potassium sorbate | 1.2 |
| Sodium saccharate | 2.0 |
| Propylene glycol | 25.0 |
| Ethyl alcohol | 15.0 |
| Methylparaben | 0.80 |
| Propylparaben | 0.20 |
| Flavors | 1.50 |
| Purified water | Ad 1 l |

Composition 5

| Components | Amount [g/L] |
| --- | --- |
| Compound of the invention | 10 |
| Saccharose | 250.0 |
| Glycerin | 50.0 |
| Sodium benzoate | 2.0 |
| Citric acid | 2.50 |
| Flavors | 1.50 |
| Purified water | Ad 1 l |

Composition 6

| Components | Ilość [g/L] |
| --- | --- |
| Compound of the invention | 10 |
| Sorbitol | 320.0 |
| Propylene glycol | 80.0 |
| Sodium citrate | 1.65 |
| Citric acid | 0.10 |
| Potassium sorbate | 1.2 |
| Flavors | 1.50 |
| Purified water | Ad 1 l |

Example 3: Biological Experiments

Materials

The below experiments were performed on male Wistar rats, at the age of 8-10 weeks, divided into two groups: the experimental group with surgically created side-to-side arterio-venous fistula between common femoral vessels (n=23) and a control group of un-operated animals (n=10). The experiment was approved by the local Bioethics Commission for experiments on animals, Warsaw 02-091, Żwirki i Wigury 61 (resolutions nr 11/2009 dated Jun. 23, 2009 and 46/12 dated Sep. 25, 2012).

Experimental Group

Rats in experimental group were divided into two sub-groups, receiving no treatment (n=14) and receiving compound of the invention (n=9). Each animal was subjected to following surgical operations.

Left Hind Limbs

After induction of general anesthesia longitudinal skin incision just below inguinal ligament was performed. Common femoral vessels were dissected from surrounding tissues proximally to the orifice of superior epigastric vessels. After application of micro-vascular clamps on common femoral vessels longitudinal 2 mm±0.1 mm long incision on antero-lateral side of the vein and antero-medial side of the artery were performed. Afterwards side-to-side anastomosis between common femoral vessels was performed to create arteriovenous fistula (non-absorbable monofilament suture 10/0). Subsequently micro-vascular clamps were removed and arteriovenous fistula patency was checked and haemostasis was achieved. To avoid lung edema, increase of blood inflow to inferior cava vein was limited by application of non-absorbable ligature of 0.9 mm internal diameter. The resultant vein lumen corresponded to approximately 80-90% of the initial vein lumen. Next, subcutaneous tissue and skin were sutured with absorbable suture.

The above procedure results in obtaining an animal model of Parkes Weber syndrome, described in the European patent application EP14001527. Hereinafter, these limbs are referred to as AVF limbs.

Right Hind Limbs

The operation of the right hind limb (control limb) included skin incision, common femoral vessels dissection, and subcutaneous and skin suture (absorbable suture). Hereinafter, these limbs are referred to as sham-operated limbs.

Control Group

Rats in the control group were also divided into two sub-groups, receiving no treatment (n=6) and receiving the compound of the invention (n=4). These animals were not subjected to any surgical procedure.

Experimental Procedure

All rats in taking part in the experiment were given ad libitum access to food and water.

Animals were fed for 1 week, than surgical procedures were conducted. After the operation, animals were fed and treated with the compound of the invention.

The rats in sub-groups receiving compound of the invention were treated for 4 weeks with the compound of the invention (E-38) in form of sodium salt (10 mg/ml, 13.7 mM) administered by oral gavage.

After 4 weeks, rats were sacrificed and measurements were conducted. Non-operated rats were fed during the whole experiment. Blood samples for serum analysis were collected before the animals were sacrificed. Biochemical analysis of the blood samples was conducted using biochemical analyzer Cobas 6000 (Roche, Hitachi).

Example 3A: Thigh Circumference, Muscle Weight, Femoral Bone Length Measurements The animals in control and experimental groups were prepared according to the method described above. The measurement phase was conducted after a 4-week treatment phase.

After euthanasia, measurements of thigh circumference limbs of animals of the experimental and control groups were performed. Soleus muscle (SOL) and the extensor digitorum longus (EDL) muscle were dissected from posterior part of hind limb, excised and weighed. Femoral bones were excised and their length was measured with an electronic slide clipper.

Statistical Analysis

The results were expressed as arithmetic means and standard errors of the mean (SEM). Statistical analysis was performed using the t-test (GraphPad Prism v.6.01). The differences at $p<0.05$ were considered statistically significant.

FIG. 1A, FIG. 1B, FIG. 2A, FIG. 2B, FIG. 3A, FIG. 3B, and FIG. 4 show data obtained for limb circumference, EDL and SOL muscle weight measurements for control and experimental groups.

Figure 2A:
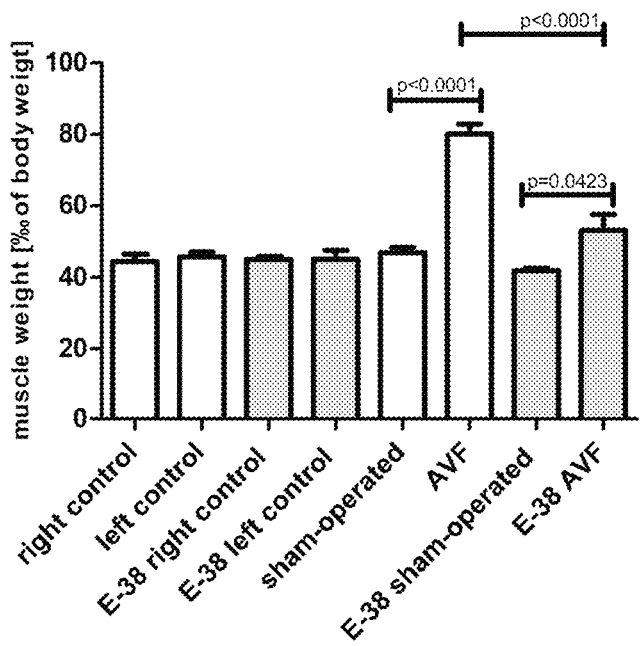
FIG. 2A shows results of measurements of EDL muscle weight in control and experimental group. The data are expressed as ‰ of animal body weight, i.e. according to the following formula: muscle weight [mg]×100/body weight [g].
Figure 2B:
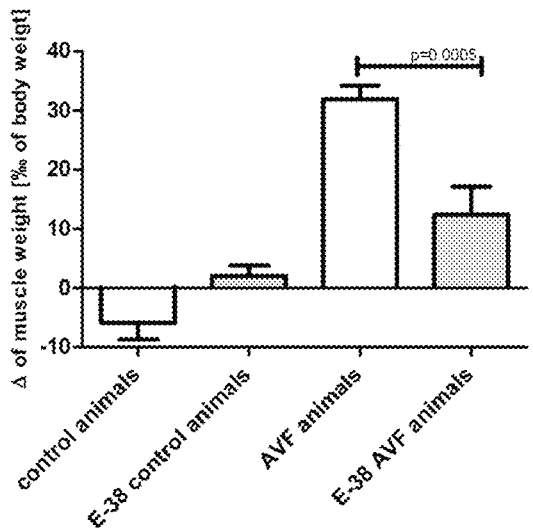
FIG. 2B shows differences between EDL muscle weight measurements (expressed as ‰ of animal body weight) for right and left hind limbs of rats in control and experimental groups.
Figure 3A:
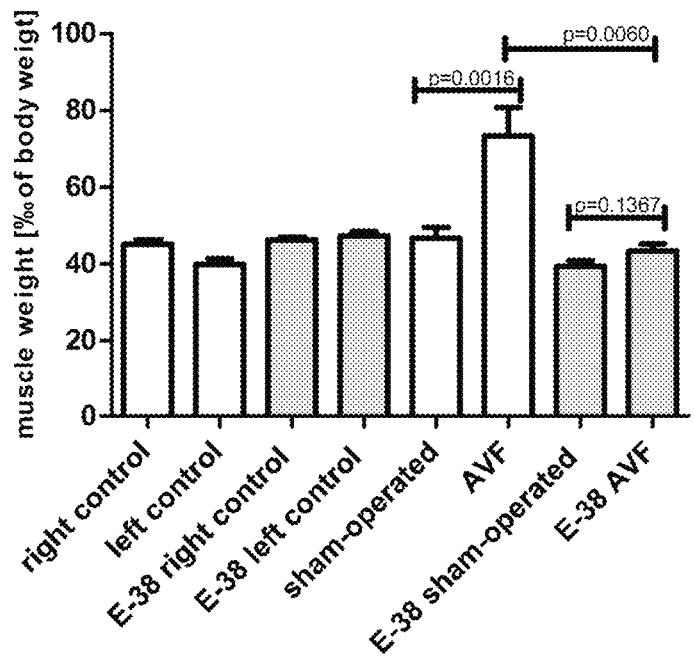
FIG. 3A shows results of measurements of SOL muscle weight in control and experimental group. The data are expressed as ‰ of animal body weight, i.e. according to the following formula: muscle weight [mg]×100/body weight [g].
Figure 3B:
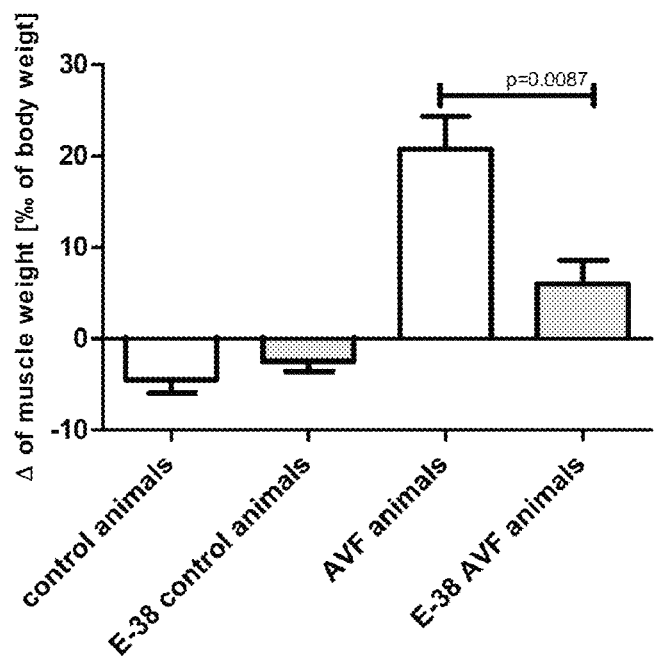
FIG. 3B shows differences between SOL muscle weight measurements (expressed as ‰ of animal body weight) for right and left hind limbs of rats in control and experimental groups.
Figure 4:
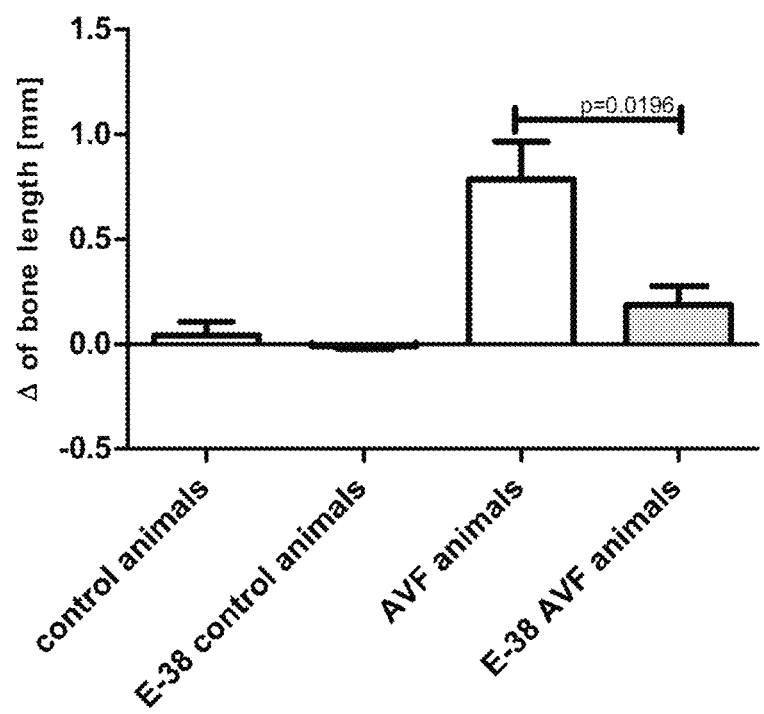
FIG. 4 shows differences between femoral bone length measurements for right and left hind limbs of rats in control and experimental groups.

In FIGS. 1A, 2A and 3A, the labels "right control" and "left control" refer to the right and left hind limb of a rat in the control group receiving no treatment, respectively. The labels "E-38 right control" and "E-38 left control" refer to the right and left hind limb of a rat in the control group receiving the compound of the invention, respectively. The label "sham operated" refers to the right hind limb of a rat in the experimental group receiving no treatment. The label "AVF" refers to the left hind limb of a rat in the experimental group receiving no treatment. The term "E-38 sham operated" refers to the right hind limb of a rat in the experimental group receiving the compound of the invention. Finally, the term "E-38 AVF" refers to the left hind limb of a rat in the experimental group receiving the compound of the invention.

In FIGS. 1B, 2B, 3B, 4, 5A, and 5B, the label "control animals" refers to rats in the control group receiving no treatment, the label "E-38-control animals" refers to rats in the control group receiving the compound of the invention, the label "AVF animals" refers to rats in the experimental group receiving no treatment, and the label "E-38 AVF animals" refers to rats in the experimental group receiving the compound of the invention.

Bars shown in FIG. 1B, FIG. 2B, FIG. 3B, and FIG. 4 depict the differences between thigh circumference, EDL muscle weight, SOL muscle weight and femoral bone length, respectively, in control and experiment rats (i.e., value measured for right limb subtracted from the value for right limb).

Data presented in FIG. 1A, FIG. 1B, FIG. 2A FIG. 2B, FIG. 3A FIG. 3B, and FIG. 4 show that treatment with the compound of the invention in the control group has insignificant influence on the measured parameters. In the experimental un-treated group, measurements show that the creation of arteriovenous fistula (AVF limbs) causes a dramatic increase of the analyzed parameters.

An increase in limb circumference, EDL and SOL muscle weights, and femoral bone length are the symptoms of venous insufficiency induced by the surgical procedure conducted on left hind limbs of rats in experimental group. FIGS. 1B, 2B, 3B, and 4 show that these symptoms were not observed in case of sham-operated limbs (right limbs) of rats in the experimental group.

Treatment with the compound of the invention resulted in reduction of the measured parameters to a very significant extent. Namely, treatment with the compound of the invention resulted in reduction of thigh circumference by approx. 12.5%, EDL muscle weight by approx. 59.2%, and SOL muscle weight by approx. 63.6% in comparison to the experimental group with no treatment (parameters for left hind limbs).

The above results confirm that the compound of the invention influences all the observed symptoms of the venous insufficiency.

Example 3B: Biochemical Analysis of the Serum Samples

In order to verify whether the administration of the compound of the invention results in any toxic effects influence in tested rats, the inventors conducted a set of basic biochemical tests of the serum isolated from the blood samples obtained from the control and experimental rats.

The conducted blood serum test included following parameters: glucose (GLUC), creatinin (CREA), urea (UREA), total protein (TP), uric acid (UA), amylase (AMYL), albumin (ALB), cholesterol (CHOL), triglicerides (TRIG), lipase (LIP), aspartate aminotransferase (AST), alanine aminotransferase (ALT), creatine kinase (CK).

Figure 5A:
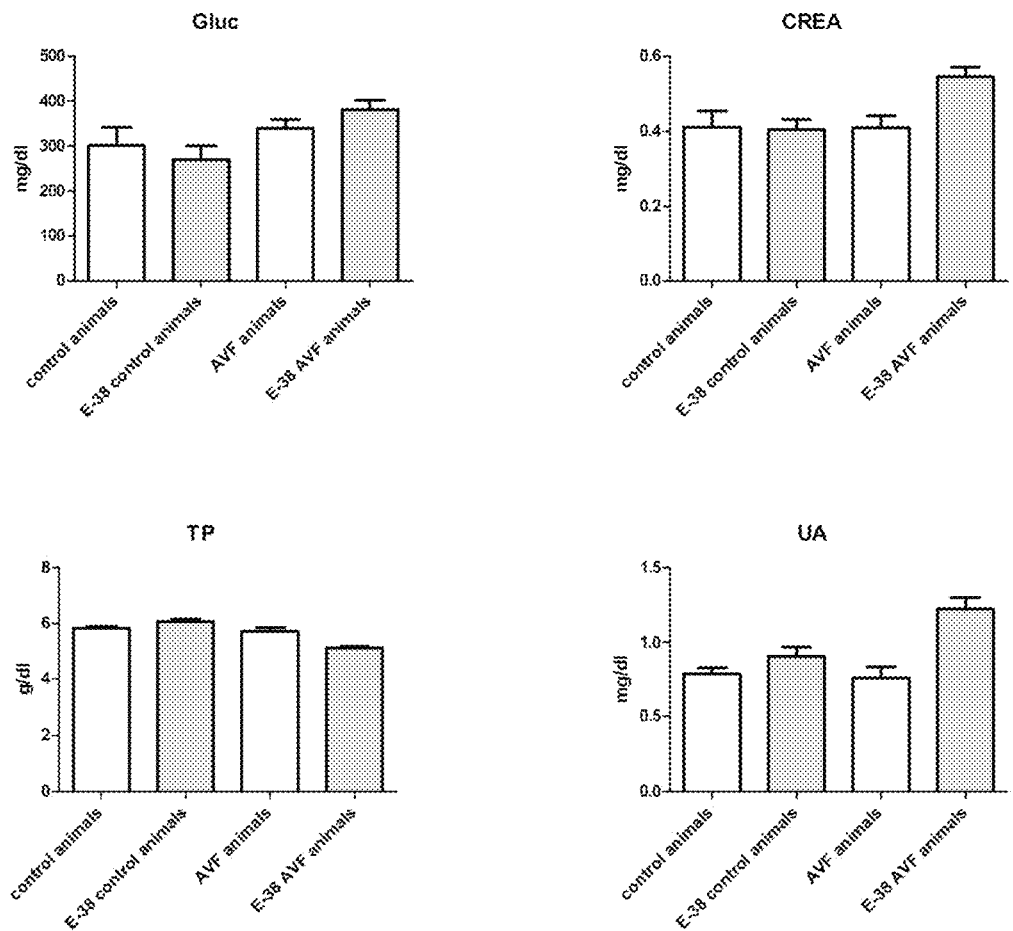
FIG. 5A, FIG. 5B, and FIG. 5C show results of biochemical analysis of the blood samples collected from rats.
Figure 5B:
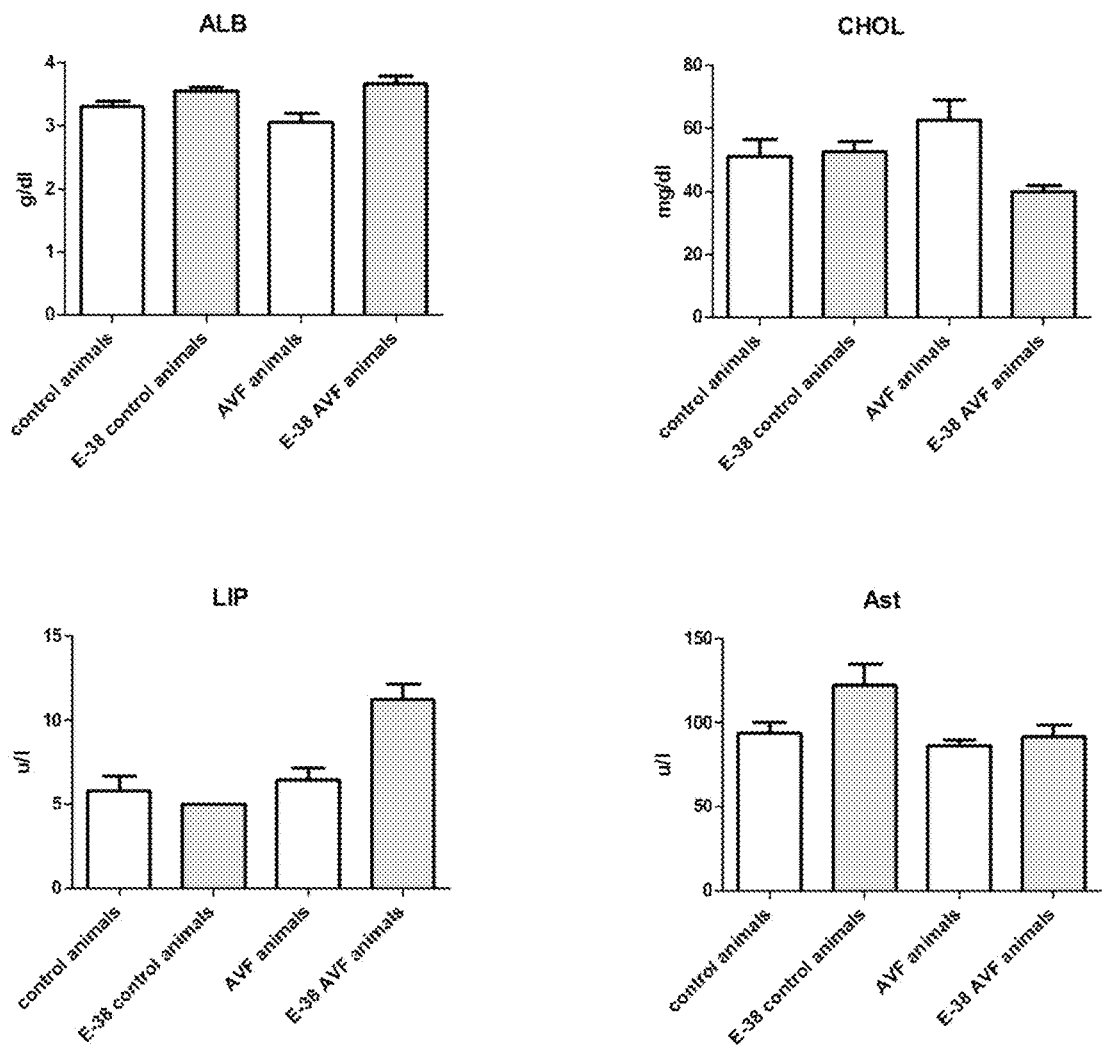
Figure 5C:
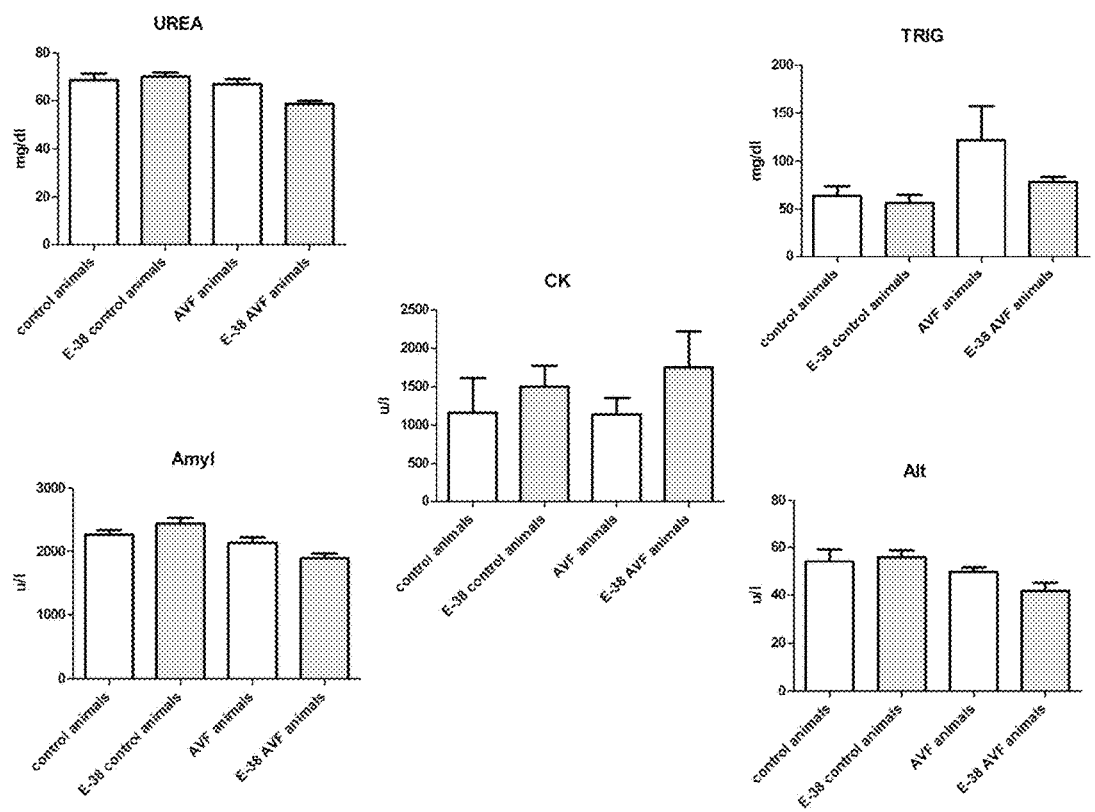

Results shown in FIGS. 5A, 5B and 5C confirm that administration of the compound of the invention has no significant influence on the blood serum parameters and which suggest that compound of the invention is a promising candidate to be used as a pharmaceutical.

Example 3C: HUVEC Experiments

In addition to the experiments described in Example 3, the compound of the invention was subjected to a test involving Human Umbilical Vein Endothelial Cells (HUVEC).

The aim of this study was to determine the cellular therapeutic efficacy of the compound of the invention in vascular inflammatory diseases. The inventors applied cellular biology tools to examine the protective effects of the compound of the invention on the vascular endothelium under inflammatory conditions.

Cell Culture

Human Umbilical Vein Endothelial Cells (HUVEC) were cultured in the EBM-2 (Lonza) supplemented with endothelial growth supplement mix (EGM-2 SingleQuot Kit Supplements and Growth Factors, Lonza) and 2% foetal bovine serum under standard cell culture condition (37° C., 5% $CO_2$). Cells were harvested using Accutase (PAA Laboratories). All described experiments were performed with cells of passage four from at least three donors. The cells were treated with the compound of the invention at 2 μM for 24 h with or without an additional of 6 h stimulation of recombinant human TNF-α (rhTNF-α, 10 ng/ml, R&D Systems).

Cell Migration Assay

The rate of cell migration was measured with the Angiogenesis System: Endothelial Cell Migration (BD Biosciences) strictly according to the manufacturer's instructions.

Vascular Permeability Assay

The In Vitro Vascular Permeability Assay Kit (Chemicon) was used to determine HUVEC monolayer permeability. All the steps of the procedure were performed according to the manufacturer's instructions.

Cell Migration Assay

The rate of cell migration was measured with Angiogenesis System: Endothelial Cell Migration (BD Biosciences). Briefly, 90% confluent HUVEC were incubated with the compound of the invention at 2 μM concentration in a complete culture medium for 24 h, then starved for 4 h in a medium containing 0.1% serum. Following seeing on migration inserts (105 cells in 250 μl of media containing the compound of the invention) HUVEC were stimulated with rhTNF-α (10 ng/ml, R&D Systems). After 22-hour incubation at 37° C., the cells on inserts were stained with Calcein AM Fluorescent Dye solution (BD Biosciences) according to the manufacturer's instructions.

Vascular Permeability Assay

The In Vitro Vascular Permeability Assay Kit (Chemicon) was used to determine HUVEC monolayer permeability following 24 h treatment of the compound of the invention at 2 μM concentrations. The effect of rhTNF-α (R&D Systems), which was added to cell culture for the last 6 h of the incubation period, was also determined. The subsequent steps of the procedure were performed according to the manufacturer's instructions.

Results

Figure 6A:
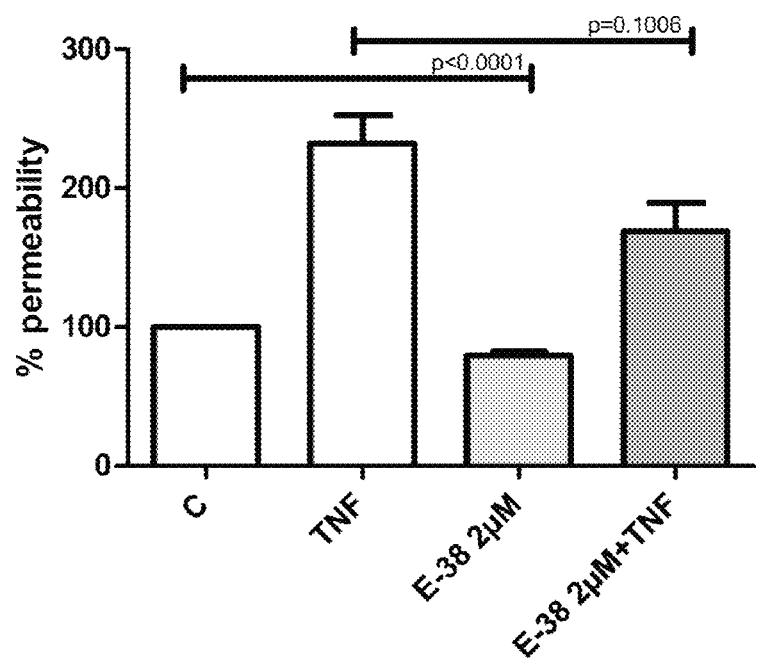
FIG. 6A shows the ratio of the permeability of HUVEC in an in vitro experiment.
Figure 6B:
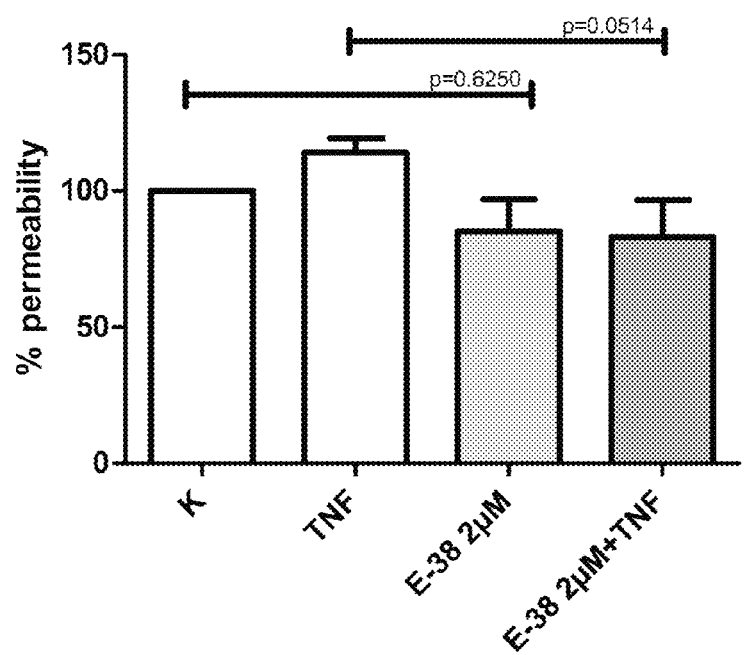
FIG. 6B shows the ratio of the migration of HUVEC in an in vitro experiment.

The result of the experiments described above are shown in FIGS. 6A and 6B.

The ability of a cell to migrate is essential in numerous vascular responses, including vascular inflammation and angiogenesis. The compound of the invention at 2 μM concentration reduced the TNF-α-induced cell migration. The integrity of the endothelial cell monolayer is one of the key conditions necessary to protect vascular homeostasis. The compound of the invention administered for 24 h at 2 μM concentration significantly decreased the TNF-α-induced endothelial cells permeability. In these in vitro experiments the inflammation process was mimicked by the addition of TNF-α to the culture media. Therefore, the reduction of the effect of TNF-α on suggests the anti-inflammatory actions of E-38 on endothelial cells.

The invention claimed is:

1. A compound of formula (I)

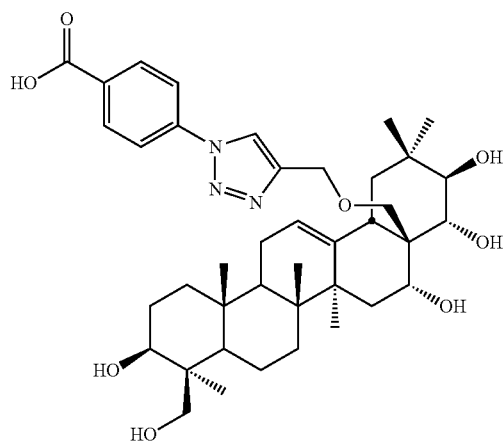

(I)

and its salts.

2. The compound according to claim 1, wherein a salt of the compound of formula (I) is a sodium salt.

3. A process for preparation of the compound according to claim 1, comprising:

a) coupling of 3,24; 16,22-O, O-diisopropylidene-28-O-propargylprotoescigenin of formula (II)

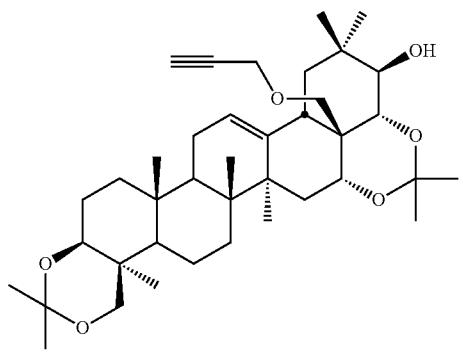

with 4-azidobenzoic acid of formula (III)
in presence of copper (I) cations generated in situ from copper (II) cation in

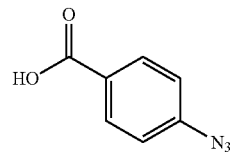

(III)

tetrahydrofuran or its mixtures with water, b) isolation of 28-O-[(1-(4-carboxyphenyl)-1H[1,2,3]triazol-4-yl)methyl]-3,24; 16,22-O,O-diisopropylideneprotoescigenin of formula (IV) from the reaction mixture,

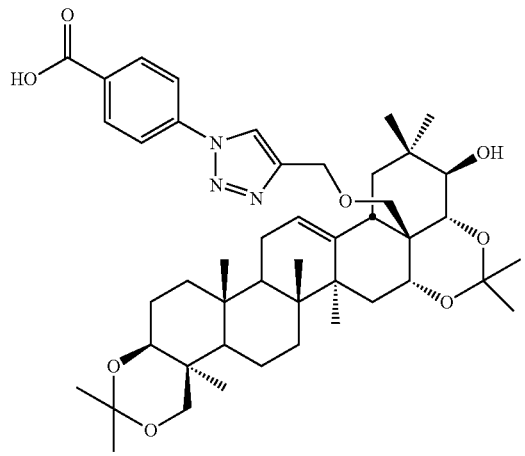

(IV)

c) purification of 28-O-[(1-(4-carboxyphenyl)-1H[1,2,3]triazol-4-yl)methyl]-3,24; 16,22-O,O-diisopropylideneprotoescigenin, d) preparation of solution or suspension of 28-O-[(1-(4-carboxyphenyl)-1H[1,2,3]triazol-4-yl)methyl]-3,24; 16,22-O,O-diisopropylideneprotoescigenin in solvent selected from group comprising C1-C3 alcohol and acetone, e) reaction with organic acid or inorganic acid and obtaining the compound of formula (I), f) isolation of the compound of formula (I), g) optional purification of the compound of formula (I), and/or optional transformation of the compound of formula (I) into its salt.

4. The process according to claim 3, wherein copper (I) cations generated in situ from copper (II) cations are obtained by reduction reaction using sodium ascorbate.

5. The process according to claim 4, wherein $CuSO_4$ is used as source of copper (II) cations.

6. The process according to claim 4, wherein the purification of 28-O-[(1-(4-carboxyphenyl)-1H[1,2,3]triazol-4-yl)methyl]-3,24;16,22-O,O-diisopropylideneprotoescigenin in step c) is carried out by maceration of said compound in methanol at a temperature ranging from 15° C. to 40° C.

7. The process according to claim 3, wherein methanol is used in step d) and p-toluenesulfonic acid is used in step e).

8. The process according to claim 3, wherein step e) is carried out at a temperature ranging from 15° C. to 60° C.

9. The process according to claim 3, wherein the optional purification in step g) is carried out in MeOH, THF, acetone or mixtures thereof.

10. The compound of claim 1, for use as a medicament.

11. A pharmaceutical composition comprising the compound of claim 1.

12. The pharmaceutical composition according to claim 11, in a formulation suitable for intravenous, oral, rectal or transdermal administration.

13. The pharmaceutical composition according to claim 11, further comprising an additional active agent.

14. The process according to claim 4, wherein the purification of 28-O-[(1-(4-carboxyphenyl)-1H[1,2,3]triazol-4-yl)methyl]-3,24;16,22-O,O-diisopropylideneprotoescigenin in step c) is carried out by maceration of said compound in methanol at a temperature ranging from 20° C. to 25° C.

15. The process according to claim 3, wherein step e) is carried out at a temperature ranging from 20° C. to 25° C.

16. A pharmaceutical composition comprising the compound of claim 1, further comprising auxiliary agents.

17. A method for treating a vascular disorder in a subject, the method comprising administering to the subject the compound of claim 1.

18. The method according to claim 17, wherein the vascular disorder is selected from the group consisting of venous insufficiency, edema, consequences of ischemia or muscles ischemia/reperfusion, pathological consequences of the presence of arteriovenous fistulas and vascular malformations.

\* \* \* \* \*